United States Patent [19]

Gehring et al.

[11] Patent Number: 4,711,658
[45] Date of Patent: Dec. 8, 1987

[54] 5-PERFLUOROACYLAMINO-4-NITRO-1-ARYLPYRAZOLE SALTS, PLANT GROWTH REGULATING AND HERBICIDAL COMPOSITION CONTAINING THEM, AND PLANT GROWTH REGULATING AND HERBICIDAL METHOD OF USING THEM

[75] Inventors: Reinhold Gehring, Wuppertal; Otto Schallner, Monheim; Jörg Stetter, Wuppertal; Hans-Joachim Santel, Leverkusen; Robert R. Schmidt; Klaus Lürssen, both of Bergisch Gladbach, all of Fed. Rep. of Germany

[73] Assignee: Bayer Aktiengesellschaft, Leverkusen, Fed. Rep. of Germany

[21] Appl. No.: 934,047

[22] Filed: Nov. 24, 1986

[30] Foreign Application Priority Data

Dec. 5, 1985 [DE] Fed. Rep. of Germany ....... 3543034

[51] Int. Cl.$^4$ .................. A01N 43/56; C07D 231/40; C07D 401/04
[52] U.S. Cl. ...................................... 71/92; 546/279; 548/376
[58] Field of Search ................ 546/279; 548/376; 71/92

[56] References Cited

FOREIGN PATENT DOCUMENTS 3402308  8/1985  Fed. Rep. of Germany ...... 548/376
3502330 12/1986  Fed. Rep. of Germany ...... 546/279
2503706 10/1982  France .............................. 548/376

*Primary Examiner*—Richard A. Schwartz
*Assistant Examiner*—Kurt G. Briscoe
*Attorney, Agent, or Firm*—Sprung Horn Kramer & Woods

[57] ABSTRACT

5-perfluoroacylamino-4-nitro-1-arylpyrazole salts of the formula

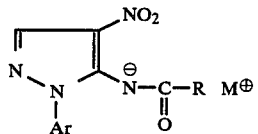

in which
R represents a perfluoroalkyl radical,
$M^\oplus$ represents one equivalent of a metal cation, or represents an optionally substituted ammonium ion and
Ar represents in each case optionally substituted phenyl or pyridyl,
exhibit herbicidal and plant growth-regulating activity.

11 Claims, No Drawings

5-PERFLUOROACYLAMINO-4-NITRO-1-ARYL-PYRAZOLE SALTS, PLANT GROWTH REGULATING AND HERBICIDAL COMPOSITION CONTAINING THEM, AND PLANT GROWTH REGULATING AND HERBICIDAL METHOD OF USING THEM

The invention relates to new 5-perfluoroacylamino-4-nitro-1-arylpyrazole salts, a process for their preparation and their use as herbicides and growth regulators.

It is already known that certain 5-halogenoacylamino-4-nitro-1-arylpyrazoles, such as, for example, 5-(ω-chlorobutyramido)-4-nitro-1-(2,6-dichloro-4-trifluoromethylphenyl)-pyrazole, have herbicidal properties (compare DE-OS (German Published Specification) No. 3,402,308).

However, the herbicidal activity of these already known compounds against problem weeds, like their tolerance towards important useful plants, is not always completely satisfactory in all fields of use.

New 5-perfluoroacylamino-4-nitro-1-arylpyrazole salts of the general formula (I)

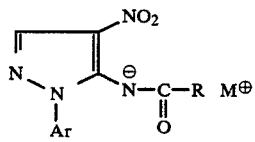

in which
R represents a perfluoroalkyl radical,
$M^\oplus$ represents one equivalent of a metal cation, or represents an optionally substituted ammonium ion and
Ar represents in each case optionally substituted phenyl or pyridyl,
have been found.

It has furthermore been found that the new 5-perfluoroacylamino-4-nitro-1-arylpyrazole salts of the general formula (I)

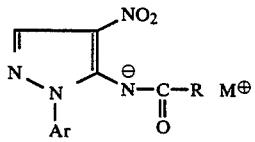

in which
R represents a perfluoroalkyl radical,
$M^\oplus$ represents one equivalent of a metal cation, or represents an optionally substituted ammonium ion and
Ar represents in each case optionally substituted phenyl or pyridyl,
are obtained by a process in which 5-perfluoroacylamino-4-nitro-1-arylpyrazoles of the formula (II)

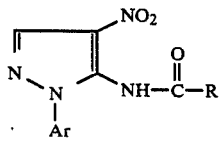

in which
R and Ar have the abovementioned meaning, are reacted with salts of the formula (III)

$$M^\oplus G^\ominus \quad \text{(III)}$$

in which
$M^\oplus$ has the abovementioned meaning and
$G^\ominus$ represents one equivalent of a suitable counter-ion,
or with primary, secondary or tertiary amines, if appropriate in the presence of a diluent.

Finally, it has been found that the new 5-perfluoroacylamino-4-nitro-1-arylpyrazole salts of the general formula (I) have a herbicidal and growth-regulating action.

Surprisingly, the 5-perfluoroacylamino-4-nitro-1-arylpyrazole salts of the general formula (I) according to the invention exhibit a considerably better herbicidal activity against problem weeds, with a comparably good selectivity for useful plants, than the 5-halogenoacylamino-4-nitro-1-arylpyrazoles known from the prior art, such as, for example, 5-(ω-chlorobutyramido)-4-nitro-1-(2,6-dichloro-4-trifluoromethylphenyl)-pyrazole, which are closely related compounds chemically and from the point of view of their action.

Formula (I) provides a general definition of the 5-perfluoroacylamino-4-nitro-1-arylpyrazole salts according to the invention. Preferred compounds of the formula (I) are those, in which
R represents a straight-chain or branched perfluoroalkyl radical with 1 to 8 carbon atoms,
$M^\oplus$ represents one equivalent of an alkali metal, alkaline earth metal or transition metal cation, or represents an ammonium ion which is optionally mono- or polysubstituted by identical or different substituents from the group comprising straight-chain or branched alkyl with 1 to 18 carbon atoms and benzyl and
Ar represents phenyl which is optionally mono- or polysubstituted by identical or different substituents, or represents 2-pyridyl, 3-pyridyl or 4-pyridyl, in each case optionally mono- or polysubstituted by identical or different substituents, possible substituents in each case being: cyano, nitro, halogen, in each case straight-chain or branched alkyl, alkoxy and alkoxy carbonyl with in each case up to 4 carbon atoms, moreover in each case straight-chain or branched halogenoalkyl and halogenalkoxy with in each case up to to 4 carbon atoms and up to 9 identical or different halogen atoms and a radical $-S(O)_m-R^1$, wherein
$R^1$ represents amino, or represents in each case straight-chain or branched alkyl, alkylamino, dialkylamino or halogenoalkyl with in each case up to 4 carbon atoms in the individual alkyl parts and, in the case of the halogenoalkyl, with up to 9 identical or different halogen atoms and
m represents the number 0, 1 or 2.

Particularly preferred compounds of the formula (I) are those in which
R represents a straight-chain or branched perfluoroalkyl radical with 1 to 4 carbon atoms,
$M^\oplus$ represents one equivalent of a sodium, potassium, magnesium, calcium, barium, copper, zinc, manganese, tin, iron, cobalt or nickel ion, or represents an ammonium ion which is optionally mono-, di-, tri- or tetrasubstituted by identical or different substituents from the group comprising straight-chain or branched alkyl with 1 to 12 carbon atoms and benzyl and Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^1$, wherein R$^1$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and m represents the number 0, 1 or 2.

The following 5-perfluoroacylamino-4-nitro-1-aryl-pyrazole salts of the general formula (I) may be mentioned specifically, in addition to the compounds mentioned in the preparation examples:

TABLE 1

| R | M$^\oplus$ | Ar |
|---|---|---|
| CF$_3$ | Na$^\oplus$ | 2,4-Cl$_2$-5-CF$_3$-phenyl |
| CF$_3$ | Na$^\oplus$ | 3-Cl-4-OCF$_3$-phenyl |
| CF$_3$ | Na$^\oplus$ | 2,4-Cl$_2$-5-SCF$_3$-phenyl |

TABLE 1-continued

| R | M$^\oplus$ | Ar |
|---|---|---|
| CF$_3$ | K$^\oplus$ | 2,4-Cl$_2$-5-CF$_3$-phenyl |
| CF$_3$ | NH$_4$$^\oplus$ | 2,4-Cl$_2$-5-CF$_3$-phenyl |
| C$_2$F$_5$ | Na$^\oplus$ | 2,4-Cl$_2$-5-CF$_3$-phenyl |
| n-C$_3$F$_7$ | Na$^\oplus$ | 2,4-Cl$_2$-5-CF$_3$-phenyl |
| n-C$_3$F$_7$ | K$^\oplus$ | 2,4-Cl$_2$-5-CF$_3$-phenyl |
| n-C$_3$F$_7$ | H$_3$N$^\oplus$—iC$_3$H$_7$ | 2,4-Cl$_2$-5-CF$_3$-phenyl |
| i-C$_3$F$_7$ | H$_3$N$^\oplus$—iC$_3$H$_7$ | 2,4-Cl$_2$-5-CF$_3$-phenyl |
| CF$_3$ | Na$^\oplus$ | 3,5-dichloro-2-pyridyl |

TABLE 1-continued $$\underset{\underset{Ar}{N}}{\overset{NO_2}{\underset{N}{\parallel}}}\overset{\ominus}{N}-\overset{O}{\underset{\parallel}{C}}-R \quad M^{\oplus} \quad (I)$$

| R | $M^{\oplus}$ | Ar |
|---|---|---|
| CF₃ | K⊕ | 2-pyridyl with CF₃ and Cl |
| CF₃ | Na⊕ | Br, CF₃-phenyl |
| CF₃ | K⊕ | Br, CF₃-phenyl |
| CF₃ | Mg²⊕ | Br, CF₃-phenyl |
| CF₃ | Ca²⊕ | Br, CF₃-phenyl |
| CF₃ | i-C₃H₇NH₃⊕ | Br, CF₃-phenyl |
| CF₃ | (C₂H₅)₃NH⊕ | Br, CF₃-phenyl |
| CF₃ | (CuOH)⊕ | Cl, Cl, CF₃-phenyl |
| CF₃ | (CuOH)⊕ | Cl, Cl, Cl, CF₃-phenyl |

If, for example, 4-nitro-5-trifluoroacetamido-1-(2,3,6-trichloro-4-trifluoromethylphenyl)-pyrazole and isopropylamine are used as starting substances, the course of the reaction in the process according to the invention can be represented by the following equation:

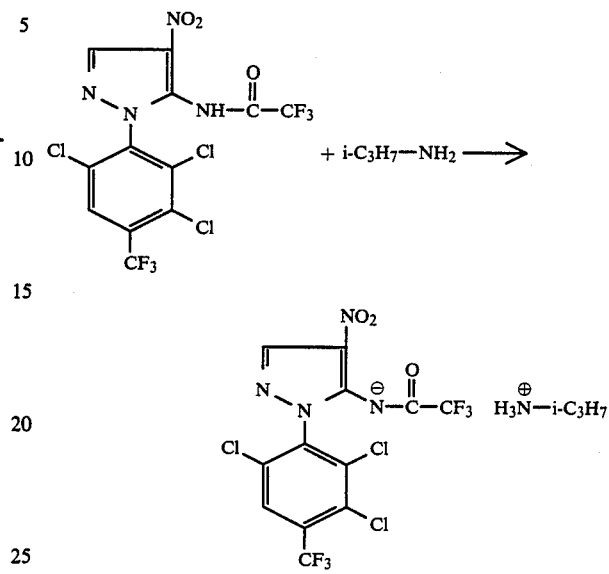

$+ \text{ i-C}_3\text{H}_7\text{—NH}_2 \longrightarrow$

Formula (II) provides a general definition of the 5-perfluoroacetamido-4-nitro-1-arylpyrazoles required as starting substances for carrying out the process according to the invention. In this formula (II), R and Ar preferably represent those radicals which have already been mentioned as preferred for these substituents in connection with the description of the substances of the formula (I) according to the invention.

The 5-perfluoroacylamino-4-nitro-1-arylpyrazoles of the formula (II) are the subject of commonly assigned German patent application DE-P No. 35 43 035, filed Dec. 5, 1985. They are obtained by a process analogous to known processes (compare, for example, DE-OS (German Published Specification) No. 3,402,308), for example by a procedure in which 5-perfluoroacylamino-1-arylpyrazoles which are unsubstituted in the 4-position, of the formula (IV)

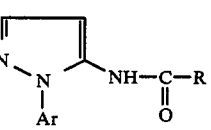

(IV)

in which

R and Ar have the abovementioned meaning, are reacted with nitric acid, if appropriate in the presence of a diluent, such as, for example, glacial acetic acid, and if appropriate in the presence of a catalyst, such as, for example, acetic anhydride, at temperatures between 20° C. and +150° C.

The 5-perfluoroacylamino-1-arylpyrazoles of the formula (IV), unsubstituted in the 4-position, are obtained by a process analogous to known processes (compare, for example, DE-OS (German Published Specification) No. 3,402,308), by a procedure in which 5-aminopyrazoles which are unsubstituted in the 4-position, of the formula (V)

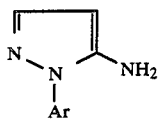 (V)

in which
Ar has the abovementioned meaning,
are acylated with fluoroacyl compounds of the formula (VI)

 (VI)

in which
R has the abovementioned meaning and
E represents an electron-attracting leaving group, such as, for example, halogen or a radical R—CO—O—, if appropriate in the presence of a diluent, such as, for example, methylene chloride, and if appropriate in the presence of an acid-binding agent, such as, for example, pyridine, at temperatures between −20° C. and +120° C.

The 5-aminopyrazoles unsubstituted in the 4-position, of the formula (V), are known (compare DE-OS (German Published Specification) No. 3,402,308), or they are the subject of commonly assigned application Ser. No. 866,638, filed May 22, 1986, now pending, corresponding to German Patent Application DE-P No. 3,520,330 of Oct. 7, 1985, and are obtainable by a process analogous to known processes (compare DE-OS (German Published Specification) No. 3,402,308), for example by a procedure in which arylhydrazines of the formula (VII)

Ar—NH—NH₂ (VII)

in which
Ar has the abovementioned meaning,
and 2-halogenoacrylonitriles of the formula (VIII)

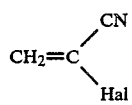 (VIII)

in which
Hal represents halogen, in particular chlorine or bromine,
are either first reacted in a first stage, if appropriate in the presence of a diluent, such as, for example, glacial acetic acid or ethanol, and if appropriate in the presence of a reaction auxiliary, such as, for example, sodium acetate, at temperatures between −20° C. and +20° C., to give the arylhydrazine derivatives of the formula (IX)

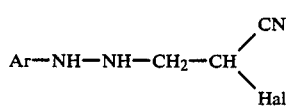 (IX)

in which
Ar and Hal have the abovementioned meaning,
and these are cyclized in a second stage, if appropriate in the presence of a diluent, such as, for example, ethylene glycol monoethyl ether, and if appropriate in the presence of an acid catalyst, such as, for example, sulphuric acid or phosphoric acid, at temperatures between +50° C. and +150° C., or are cyclized directly in one reaction step, without isolation of the intermediate of the formula (IX), if appropriate in the presence of a diluent, such as, for example, ethylene glycol monoethyl ether or ethanol, at temperatures between +50° C. and +150° C.

The arylhydrazines of the formula (VII) are known (compare, for example, U.S. Pat. No. 4,127,575; U.S. Pat. No. 3,609,158; DE-OS (German Published Specification) No. 2,558,399; and J. Chem. Soc. C, 1971, 167–174), or they can be obtained by known processes in a simple analogous manner (compare, for example, Houben-Weyl "Methoden der organischen Chemie" ("Methods of organic chemistry") Volume X/2, page 203, Thieme Verlag Stuttgart, 1967), by a procedure in which, for example, the known anilines or pyridylamines of the formula (X)

Ar—NH₂ (X)

in which
Ar has the abovementioned meaning,
are reacted with sodium nitrite in the presence of an acid, such as, for example, sulphuric acid, and then with tin-II chloride, likewise in the presence of an acid, such as, for example, hydrochloric acid, at temperatures between −20° C. and +80° C., or by a procedure in which halogenoaromatics of the formula (XI)

Ar—Hal¹ (XI)

in which
Ar has the abovementioned meaning and
Hal¹ represents halogen, in particular fluorine, chlorine or bromine,
are reacted with hydrazine hydrate, if appropriate in the presence of a diluent, such as, for example, pyridine or dioxane, at temperatures between 0° C. and 150° C.

The fluoroacyl compounds of the formula (VI), the 2-halogenoacrylonitriles of the formula (VIII), the anilines and pyridylamines of the formula (X) and the halogenoaromatics of the formula (XI) are generally known compounds of organic chemistry.

Possible diluents for carrying out the process according to the invention are polar organic solvents, water or aqueous mixtures. Alcohols, such as, for example, methanol, ethanol or propanol, aqueous mixtures thereof or pure water are preferably used.

The reaction temperatures can be varied within a substantial range in carrying out the process according to the invention. The reaction is in general carried out between 0° C. and +80° C., preferably between +20° C. and +40° C.

For carrying out the process according to the invention, in general 1.0 to 10 mols, preferably 1.0 to 5.0 mols, of salt-forming agent of the formula (III) or amine are employed per mol of 5-perfluoroacylamino-4-nitro-1-arylpyrazole of the formula (II).

To prepare the sodium, potassium or ammonium salts, a compound of the formula (II) is reacted in aqueous solution or an organic solvent, such as acetone, methanol, ethanol or dimethylformamide, with sodium hydroxide, potassium hydroxide or ammonium hydroxide or an amine and the salts are isolated by filtration or by evaporation of the solution, and, if appropriate, purified by recrystallization.

The calcium, barium, magnesium, manganese, copper, nickel, tin, iron and cobalt salts are prepared from the sodium salts by treatment with a corresponding inorganic metal salt, for example calcium chloride, barium chloride, copper sulphate, nickel chloride or cobalt nitrate. The calcium salts can also be prepared by treatment of a compound of the formula (II) with calcium hydroxide.

The active compounds according to the invention can be used as defoliants, desiccants, agents, for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds, in particular in monocotyledon crops, such as barley and wheat.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and on the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, suspension-emulsion concentrates, foams, natural and synthetic materials impregnated with active compound, and very fine capsules in polymeric substances and in coating compositions for seed, as well as ULV formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl or cyclohexanone, strongly polar solvents, such as dimethylformamide and dimethylsulphoxide, as well as water. By liquefied gaseous extenders or carriers are meant those liquids which are gaseous at normal temperature and under normal pressure, for example aerosol propellants, such as halogenohydrocarbons as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used as herbicides, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beets, and 4-amino-6-(1,1-dimethylethyl)-3-methylthio-1,2,4-triazin-5(4H)-one for combating weeds in soy beans.

Mixtures with N,N-dimethyl-N'-(3-chloro-4-methylphenyl)-urea; N,N-dimethyl-N'-(4-isopropylphenyl)urea; 4-amino-6-t-butyl-3-ethylthio-1,2,4-triazin-5-(4H)-one; 2,4-dichlorophenoxy acetic acid; 2,4-dichlorophenoxypropionic acid; (2-methyl-4-chlorophenoxy)-acetic acid; (4-chloro-2-methylphenoxy)-propionic acid; 2-benzyloxyethyl, trimethylsilylmethyl or 2,2-diethoxyethyl 2-[4-(3,5-dichloropyrid-2-yloxy)-phenyl]-propionate; methyl 5-(2,4-dichlorophenoxy)-2-nitrobenzoate; 3,5-diiodo-4-hydroxybenzonitrile; 3-isopropyl-2,1,3-benzothiadiazine-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-s-triazine; N-methyl-2-(1,3-benzothiazol-2-yloxy)-acetanilide; S-(2,3,3-trichloroallyl) N,N-diisopropyl-thiolcarbamate; N-(1-ethylpropyl)-3,4-dimethyl-2,6-dinitroaniline,3,5-dibromo-4-hydroxybenzonitrile; and methyl 2-[4-(2,4-dichlorophenoxy)-phenoxy]-propionate, where appropriate, are also of advantage.

Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation of the active compound itself into the soil. It is also possible to treat the seeds of plants.

The amounts applied can be varied within a substantial range. In general, 0.01 to 50 kg, preferably 0.05 to 10 kg, of active compound are used per hectare of soil surface.

As regards the time of application, the rule is that the growth regulators are applied within a preferred period of time, the exact definition of which depends on the climatic and vegetative circumstances.

The preparation and use of the active compounds according to the invention can be seen from the following examples.

PREPARATION EXAMPLES

EXAMPLE 1

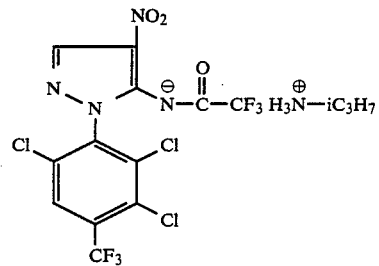

1.1 ml (0.012 mol) of anhydrous isopropylamine are added dropwise to 4.0 g (0.0085 mol) of 4-nitro-5-trifluoroacetamido-1-(2,3,6-trichloro-4-trifluoromethylphenyl)pyrazole in 40 ml of ethanol, while stirring. The solvent is distilled off in vacuo and the oily residue is rubbed in with 20 ml of methylene chloride. After the solvent has been evaporated off in vacuo, 4.3 g (93% of theory) of 4-nitro-5-trifluoroacetamido-1-(2,3,6-trichloro-4-trifluoromethylphenyl)-pyrazole isopropylammonium salt of melting point 192° C.–193° C. are obtained.

PREPARATION OF THE STARTING COMPOUND

EXAMPLE II-1

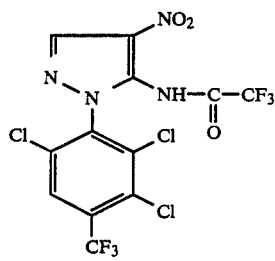

2.4 ml (0.0258 mol) of acetic anhydride and 1.1 ml (0.025 mol) of 98% strength nitric acid are added in succession to 10 g (0.0235 mol) of 5-trifluoroacetamido-1-(2,3,6-trichloro-4-trifluoromethylphenyl)-pyrazole in 20 ml of glacial acetic acid at room temperature. After the mixture has been stirred for 20 hours, it is concentrated in vacuo, the residue is taken up in 100 ml of methylene chloride and the mixture is extracted with 400 ml of 5% strength aqueous sodium carbonate solution. The aqueous phase is acidified and extracted with 200 ml of methylene chloride. The combined organic phases are dried over magnesium sulphate and freed from the solvent in vacuo. 8.6 g (77.6% of theory) of 4-nitro-5-trifluoroacetamido-1-(2,3,6-trichloro-4-trifluoromethylphenyl)-pyrazole of melting point 136° C.–137° C. are obtained.

EXAMPLE IV-1

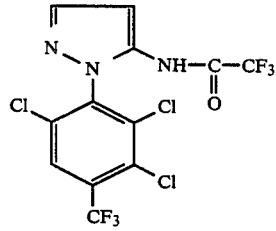

3.1 ml (0.039 mol) of anhydrous pyridine and 5.5 ml (0.038 mol) of trifluoroacetic anhydride are added in succession to 12 g (0.0363 mol) of 5-amino-1-(2,3,6-trichloro-4-trifluoromethylphenyl)-pyrazole in 65 ml of methylene chloride at 0° to 5° C., while stirring. For working up, 50 ml of methylene chloride are added, the mixture is washed in succession with dilute hydrochloric acid and aqueous sodium bicarbonate and sodium chloride solution, the organic phase is dried over magnesium sulphate and the solvent is removed in vacuo. 14.6 g (94.3% of theory) of 5-trifluoroacetamido-1-(2,3,6-trichloro-4-trifluoromethylphenyl)-pyrazole of melting point 145° C. are obtained.

EXAMPLE 2

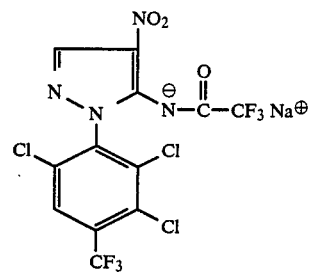

An aqueous solution of 0.53 g (0.00636 mol) of sodium bicarbonate is slowly added to 3.0 g (0.00636 mol) of 4-nitro-5-trifluoroacetamido-1-(2,3,6-trichloro-4-trifluoromethylphenyl)-pyrazole in 40 ml of ethanol. When the addition has ended, the mixture is warmed at the reflux temperature for 30 minutes, the cooled reaction mixture is filtered and the filtrate is concentrated in vacuo. The glassy residue is titurated with 50 ml of methylene chloride and the mixture is concentrated again in vacuo. 3.0 g (95% of theory) of 4-nitro-5-trifluoroacetamido-1-(2,3,6-trichloro-4-trifluoromethylphenyl)-pyrazole sodium salt of melting point 118° C.–121° C. are obtained.

The following 5-perfluoroacylamino-4-nitro-1-arylpyrazole salts of the general formula (I) are obtained in a corresponding manner and in accordance with the general statements on the preparation:

TABLE 2

| Exmp. No. | R | $M^{\oplus}$ | Ar | Melting point/°C. |
|---|---|---|---|---|
| 3 | $CF_3$ | $H_3\overset{\oplus}{N}-iC_3H_7$ | 2-Cl, 4-OCF$_3$-phenyl | 109–117 |
| 4 | $CF_3$ | $K^{\oplus}$ | 2,3,6-Cl$_3$, 4-CF$_3$-phenyl | 121 |
| 5 | $CF_3$ | $H_3\overset{\oplus}{N}-iC_3H_7$ | 2-Cl, 5-Br, 4-CF$_3$-phenyl | 169–173 |
| 6 | $CF_3$ | $(MgOH)^{\oplus}$ | 2,3,6-Cl$_3$, 4-CF$_3$-phenyl | 128–130 |
| 7 | $CF_3$ | $H_3\overset{\oplus}{N}-iC_3H_7$ | 2-Br, 4-CF$_3$-phenyl | |

TABLE 2-continued

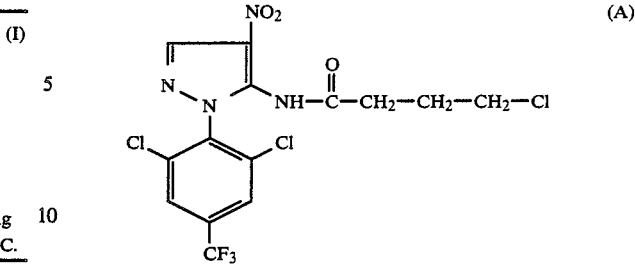

(I)

| Exmp. No. | R | M⊕ | Ar | Melting point/°C |
|---|---|---|---|---|
| 8 | $CF_3$ | $(ZnOH)^⊕$ | 2,6-Cl,Cl-4-$CF_3$-phenyl | >250° C. |
| 9 | $CF_3$ | $(MnOH)^⊕$ | 2,6-Cl,Cl-4-$CF_3$-phenyl | >250° C. |
| 10 | $CF_3$ | $H_3\overset{⊕}{N}-(CH_2)_5-CH_3$ | 2-Cl,6-F-4-$CF_3$-phenyl | 120–125 |
| 11 | $CF_3$ | $H-\overset{⊕}{N}(C_2H_5)_3$ | 2-Cl,6-F-4-$CF_3$-phenyl | 102–106 |
| 12 | $CF_3$ | $NH_4^⊕$ | 2-Cl,6-F-4-$CF_3$-phenyl | 128–145 |
| 13 | $CF_3$ | $H_3\overset{⊕}{N}-(CH_2)_5-CH_3$ | 2,6-Cl,Cl-4-$CF_3$-phenyl | 171–174 |
| 14 | $CF_3$ | $H-\overset{⊕}{N}(C_2H_5)_3$ | 2,6-Cl,Cl-4-$CF_3$-phenyl | 110–113 |
| 15 | $CF_3$ | $H_3\overset{⊕}{N}-iC_3H_7$ | 2-Cl,6-F-4-$CF_3$-phenyl | 182–187 |

USE EXAMPLES

The compound shown below was employed as the comparison substance in the use examples which follow:

(A)

[Structure: 5-(ω-chlorobutyramido)-4-nitro-1-(2,6-dichloro-4-trifluoromethylphenyl)-pyrazole]

5-(ω-chlorobutyramido)-4-nitro-1-(2,6-dichloro-4-trifluoromethylphenyl)-pyrazole (known from DE-OS (German Published Specification) No. 3,402,308).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to preparation Examples 1, 2, 13, 14 and 15 exhibit a clearly better herbicidal acitivity against weeds, such as, for example Ipomoea, Sinapis and Stellaria, and a better compatibility for useful plants, such as, for example, barley and wheat, than the comparison substance (A).

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)

100%=total destruction

In this test, for example, the compounds according to preparation Examples 1, 2 and 15 exhibit a clearly better herbicidal activity against weeds, such as, for example, Chenopodium, Matricaria, Sinapis and Stellaria and a better compatibility for useful plants, such as, for example, wheat, than the comparison substance (A).

EXAMPLE C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparation of active compound until dripping wet. After 1 week, the shedding of leaves and the desiccation of the leaves are rated, in comparison with the control plants.

In this test, for example, the compound according to preparation Example 1 shows a clearly greater activity in comparison with the untreated control.

It is understood that the specification and examples are illustrative but not limitative of the present invention and that other embodiments within the spirit and scope of the invention will suggest themselves to those skilled in the art.

What is claimed is:

1. A 5-perfluoroacylamino-4-nitro-1-arylpyrazole salt of the formula

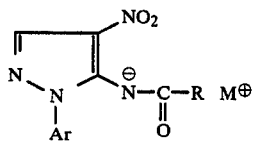

in which
R represents a straight-chain or branched perfluoroalkyl radical with 1 to 8 carbon atoms,
$M^\oplus$ represents one equivalent of an alkali metal, alkaline earth metal or transition metal cation, or represents an ammonium ion which is optionally mono-, di-, tri- or polysubstituted by identical or different substituents from the group consisting of straight-chain or branched alkyl with 1 to 18 carbon atoms and benzyl and
Ar represents phenyl which is optionally mono- or polysubstituted by identical or different substituents, or represents 2o-pyridyl, 3-pyridyl or 4-pyridyl, in each case optionally mono- or polysubstituted by identical or different substituents, possible substituents in each case being selected from the group consisting of cyano, nitro, halogen, in each case straight-chain or branched alkyl, alkoxy and alkoxycarbonyl with in each case up to 4 carbon atoms, in each case straight-chain or branched halogenoalkyl and halogenoalkoxy with in each case up to 4 carbon atoms and up to 9 identical or different halogen atoms and a radical $-S(O)_m-R^1$, wherein
$R^1$ represents amino, or represents in each case straight-chain or branched alkyl, alkylamino, dialkylamino or halogenoalkyl with in each case up to 4 carbon atoms in the individual alkyl parts and, in the case of the halogenoalkyl, with up to 9 identical or different halogen atoms and
m represents the number 0, 1 or 2.

2. A 5-perfluoroacylamino-4-nitro-1-arylpyrazole salt according to claim 1, in which
R represents a straight-chain or branched perfluoroalkyl radical with 1 to 4 carbon atoms,
$M^\oplus$ represents one equivalent of a sodium, potassium, magnesium, calcium, barium, copper, zinc, manganese, tin, iron, cobalt or nickel ion, or represents an ammonium ion which is optionally mono-, di-, tri- or tetrasubstituted by identical or different substituents from the group consisting of straight-chain or branched alkyl with 1 to 12 carbon atoms and benzyl and Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents in each case being selected from the group consisting of cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical $-S(O)_m-R^1$, wherein
$R^1$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and
m represents the number 0, 1 or 2.

3. A salt according to claim 1, wherein such salt is 4-nitro-5-trifluoroacetamido-1-(2,3,6-trichloro-4-trifluoromethylphenyl)pyrazole-isopropylammonium salt of the formula

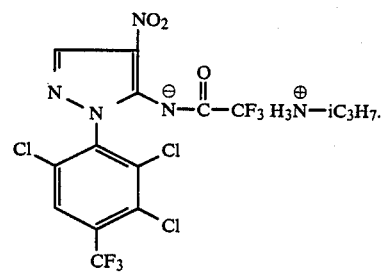

4. A salt according to claim 1, wherein such salt is 4-nitro-5-trifluoroacetamido-1-(2,3,6-trichloro-4-trifluoromethylphenyl)-pyrazole sodium salt of the formula

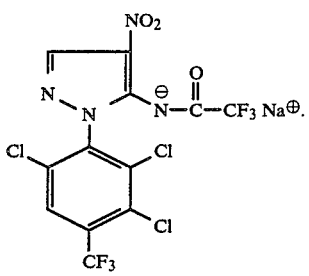

5. A salt according to claim 1 wherein such salt is 4-nitro-5-trifluoroacetamido-1-(2,3,6-trichloro-4-trifluoromethylphenyl)-pyrazole potassium salt of the formula

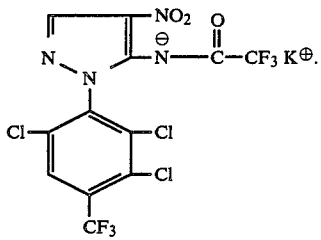

6. A salt according to claim 1, wherein such salt is 4-nitro-5-trifluoroacetamido-1-(2,3,6-trichloro-4-trifluoromethylphenyl)-pyrazole-n-hexylammonium salt of the formula

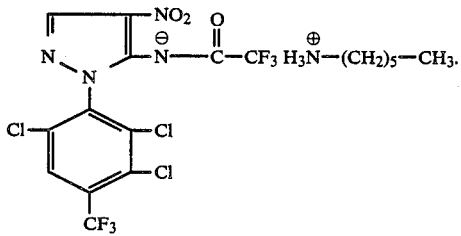

7. A salt according to claim 1, wherein such salt is 4-nitro-5-trifluoroacetamido-1-(2,3,6-trichloro-4-trifluoromethylphenyl)-pyrazole-triethylammonium salt of the formula

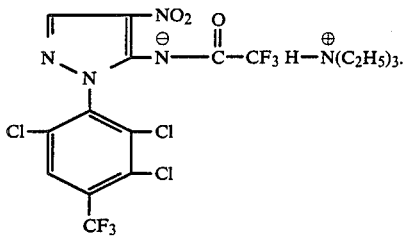

8. A salt according to claim 1 wherein such salt is 4-nitro-5-trifluoroacetamido-1-(2,6-dichloro-3-fluoro-4-trifluoromethylphenyl)-pyrazole-isopropylammonium salt of the formula

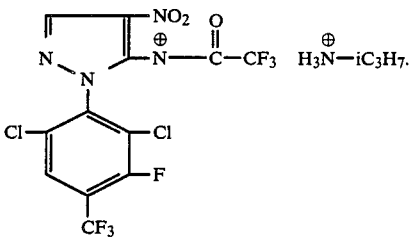

9. A plant growth regulating or herbicidal composition comprising an amount effective therefor of a salt according to claim 1 and a diluent.

10. A method of killing or regulating the growth of plants which comprises applying to such plants or to a locus in which such plants are grown or to be grown an amount effective therefor of a salt according to claim 1.

11. The method according to claim 10, wherein such salt is
4-nitro-5-trifluoroacetamido-1-(2,3,6-trichloro-4-trifluoromethylphenyl)-pyrazole isopropyl ammonium salt,
4-nitro-5-trifluoroacetamideo-1-(2,3,6-trichloro-4-trifluoromethylphenyl)-pyrazole sodium salt,
4-nitro-5-trifluoroacetamido-1-(2,3,6-trichloro-4-trifluoromethylphenyl)-pyrazole potassium salt,
4-nitro-5-trifluoroacetamido-1-(2,3,6-trichloro-4-trifluoromethylphenyl)-pyrazole-n-hexylammonium salt,
4-nitro-5-trifluoroacetamido-1-(2,3,6-trichloro-4-trifluoromethylphenyl)-pyrazole-triethylammonium salt or
4-nitro-5-trifluoroacetamido-1-(2,6-dichloro-3-fluoro-4-trifluoromethylphenyl)-pyrazole-isopropylammonium salt.

* * * * *

UNITED STATES PATENT AND TRADEMARK OFFICE
CERTIFICATE OF CORRECTION

PATENT NO.  : 4,711,658
DATED       : December 8, 1987
INVENTOR(S) : Reinhold Gehring, et al.

It is certified that error appears in the above-identified patent and that said Letters Patent is hereby corrected as shown below:

| | |
|---|---|
| Col. 10, line 42 | After "isobutyl" insert --ketone-- |
| Col. 17, line 22 | Delete "preparation" and substitute --preparations-- |
| Col. 17, line 57 | Delete "2o-" and substitute -- 2- -- |
| Col. 18, line 51 | After ")" insert -- - -- |
| Col. 20, line 20 | Right side of formula delete "N" and substitute $\overset{\ominus}{N}$ |
| Col. 20, line 40 | Correct spelling of --trifluoroacetamido-- |

Signed and Sealed this

Second Day of August, 1988

Attest:

DONALD J. QUIGG

Attesting Officer

Commissioner of Patents and Trademarks